(12) United States Patent
Burnell

(10) Patent No.: US 8,939,958 B2
(45) Date of Patent: *Jan. 27, 2015

(54) FLUID TRANSFER ASSEMBLY FOR A SYRINGE

(75) Inventor: Rosemary Louise Burnell, Blinco Grove (GB)

(73) Assignee: Cilag GmbH International (CH)

( * ) Notice: Subject to any disclaimer, the term of this patent is extended or adjusted under 35 U.S.C. 154(b) by 70 days.

This patent is subject to a terminal disclaimer.

(21) Appl. No.: 12/997,684

(22) PCT Filed: Jun. 10, 2009

(86) PCT No.: PCT/GB2009/001446
§ 371 (c)(1),
(2), (4) Date: Dec. 13, 2010

(87) PCT Pub. No.: WO2009/153541
PCT Pub. Date: Dec. 23, 2009

(65) Prior Publication Data
US 2011/0098670 A1    Apr. 28, 2011

(30) Foreign Application Priority Data

Jun. 19, 2008 (GB) .................................. 0811343.3

(51) Int. Cl.
| A61M 5/178 | (2006.01) |
| A61M 5/32 | (2006.01) |
| A61M 5/20 | (2006.01) |
| A61J 1/20 | (2006.01) |

(52) U.S. Cl.
CPC ............... *A61M 5/20* (2013.01); *A61J 1/2096* (2013.01); *A61J 2001/201* (2013.01); *A61M 5/326* (2013.01)

USPC ........... 604/414; 604/403; 604/411; 604/412; 604/413; 604/415

(58) Field of Classification Search
None
See application file for complete search history.

(56) References Cited

U.S. PATENT DOCUMENTS

| 1,845,036 A | 2/1932 | Busher |
| 2,019,382 A | 10/1935 | Aronson |
| 2,531,267 A | 11/1950 | Harnisch |
| 2,764,977 A | 10/1956 | Ferguson |
| 2,828,742 A | 4/1958 | Ashkenaz |
| 3,320,955 A | 5/1967 | Sarnoff |
| 3,329,146 A | 7/1967 | Waldman |

(Continued)

FOREIGN PATENT DOCUMENTS

| CH | 518102 A | 1/1972 |
| CN | 2059579 U | 7/1990 |

(Continued)

OTHER PUBLICATIONS

International Search Report dated Sep. 5, 2005; International Application No. PCT/GB2005/002131.

(Continued)

*Primary Examiner* — Oren Ginsberg
*Assistant Examiner* — Joshua Lee

(57) ABSTRACT

A fluid transfer assembly comprise a first open end for connection to a syringe and a second open end for receiving a vial having a closure element. The second open end is adapted to engage and open the closure element and permit fluid in the vial to be transferred to the syringe from the vial, for example by gravity acting on the fluid in the vial.

2 Claims, 4 Drawing Sheets

(56) References Cited

U.S. PATENT DOCUMENTS

| | | | |
|---|---|---|---|
| 3,543,603 A | 12/1970 | Gley | |
| 3,656,472 A | 4/1972 | Moura | |
| 3,702,608 A | 11/1972 | Tibbs | |
| 3,742,948 A | 7/1973 | Post et al. | |
| 3,797,488 A | 3/1974 | Hurschman et al. | |
| 3,797,489 A | 3/1974 | Sarnoff | |
| 3,880,163 A | 4/1975 | Ritterskamp | |
| 3,976,069 A | 8/1976 | Ong | |
| 4,165,739 A | 8/1979 | Doherty et al. | |
| 4,180,070 A | 12/1979 | Genese | |
| 4,185,628 A | 1/1980 | Kopfer | |
| 4,194,505 A | 3/1980 | Schmitz | |
| 4,222,380 A | 9/1980 | Terayama | |
| 4,231,368 A | 11/1980 | Becker | |
| 4,236,516 A | 12/1980 | Nilson | |
| 4,299,238 A | 11/1981 | Baidwan et al. | |
| 4,333,459 A | 6/1982 | Becker | |
| 4,378,015 A | 3/1983 | Wardlaw | |
| 4,394,863 A | 7/1983 | Bartner | |
| 4,403,989 A | 9/1983 | Christensen et al. | |
| 4,407,283 A | 10/1983 | Reynolds | |
| 4,425,120 A | 1/1984 | Sampson et al. | |
| 4,430,082 A | 2/1984 | Schwabacher | |
| 4,521,237 A | 6/1985 | Logothetis | |
| 4,561,856 A | 12/1985 | Cochran et al. | |
| 4,636,201 A | 1/1987 | Ambrose et al. | |
| 4,639,250 A | 1/1987 | Rycroft | |
| 4,642,099 A | 2/1987 | Phillips et al. | |
| 4,676,530 A | 6/1987 | Nordgren et al. | |
| 4,744,786 A | 5/1988 | Hooven et al. | |
| 4,787,891 A | 11/1988 | Levin et al. | |
| 4,874,383 A | 10/1989 | McNaughton | |
| 4,874,384 A | 10/1989 | Nunez | |
| 4,929,232 A | 5/1990 | Sweeney et al. | |
| 4,969,870 A | 11/1990 | Kramer et al. | |
| 4,988,339 A | 1/1991 | Vadher | |
| 5,009,646 A | 4/1991 | Sudo et al. | |
| 5,026,349 A | 6/1991 | Schmitz et al. | |
| 5,057,079 A | 10/1991 | Tiemann et al. | |
| 5,092,842 A | 3/1992 | Bechtold et al. | |
| 5,098,400 A | 3/1992 | Crouse et al. | |
| 5,112,119 A | 5/1992 | Cooke et al. | |
| 5,114,406 A | 5/1992 | Gabriel et al. | |
| 5,122,119 A | 6/1992 | Lucas | |
| 5,137,516 A | 8/1992 | Rand et al. | |
| 5,141,496 A | 8/1992 | Dalto et al. | |
| 5,147,325 A | 9/1992 | Mitchell et al. | |
| 5,156,599 A | 10/1992 | Ranford et al. | |
| 5,176,643 A | 1/1993 | Kramer et al. | |
| 5,190,526 A | 3/1993 | Murray et al. | |
| 5,242,416 A | 9/1993 | Hutson | |
| 5,250,026 A | 10/1993 | Ehrlich et al. | |
| 5,250,037 A | 10/1993 | Bitdinger | |
| 5,263,933 A | 11/1993 | Novacek et al. | |
| 5,267,963 A | 12/1993 | Bachynsky | |
| 5,271,744 A | 12/1993 | Kramer et al. | |
| 5,295,965 A | 3/1994 | Wilmot | |
| 5,300,030 A | 4/1994 | Crossman et al. | |
| 5,312,364 A | 5/1994 | Jacobs | |
| 5,330,081 A | 7/1994 | Davenport | |
| 5,330,430 A | 7/1994 | Sullivan | |
| 5,358,489 A | 10/1994 | Wyrick | |
| 5,364,369 A * | 11/1994 | Reynolds | 604/187 |
| 5,368,577 A | 11/1994 | Teoh et al. | |
| 5,372,586 A | 12/1994 | Haber et al. | |
| 5,391,151 A | 2/1995 | Wilmot | |
| 5,405,362 A | 4/1995 | Kramer et al. | |
| 5,411,488 A | 5/1995 | Pagay et al. | |
| 5,425,715 A | 6/1995 | Dalling et al. | |
| 5,451,210 A | 9/1995 | Kramer et al. | |
| 5,478,316 A | 12/1995 | Bitdinger et al. | |
| 5,480,387 A | 1/1996 | Gabriel et al. | |
| 5,487,732 A | 1/1996 | Jeffrey | |
| 5,489,256 A | 2/1996 | Adair | |
| 5,503,627 A | 4/1996 | McKinnon et al. | |
| 5,514,097 A | 5/1996 | Knauer | |
| 5,520,653 A | 5/1996 | Reilly et al. | |
| 5,540,660 A | 7/1996 | Jenson et al. | |
| 5,540,666 A | 7/1996 | Barta et al. | |
| 5,540,709 A | 7/1996 | Ramel et al. | |
| 5,567,160 A | 10/1996 | Massino | |
| 5,569,191 A | 10/1996 | Meyer | |
| 5,569,192 A | 10/1996 | van der Wal | |
| 5,575,777 A | 11/1996 | Cover et al. | |
| 5,599,302 A | 2/1997 | Lilley et al. | |
| 5,599,309 A | 2/1997 | Marshall et al. | |
| 5,607,395 A | 3/1997 | Ragsdale et al. | |
| 5,609,577 A | 3/1997 | Haber et al. | |
| 5,609,584 A | 3/1997 | Gettig et al. | |
| 5,611,785 A | 3/1997 | Mito et al. | |
| 5,637,094 A | 6/1997 | Stewart, Jr. et al. | |
| 5,645,536 A | 7/1997 | Whisson | |
| 5,647,845 A | 7/1997 | Haber et al. | |
| 5,658,259 A | 8/1997 | Pearson et al. | |
| 5,665,071 A | 9/1997 | Wyrick | |
| 5,681,291 A | 10/1997 | Galli | |
| 5,697,908 A | 12/1997 | Imbert | |
| 5,702,367 A | 12/1997 | Cover et al. | |
| 5,704,911 A | 1/1998 | Parsons et al. | |
| 5,709,662 A | 1/1998 | Olive et al. | |
| 5,713,866 A | 2/1998 | Wilmot | |
| 5,748,316 A | 5/1998 | Wakabayashi et al. | |
| 5,779,668 A | 7/1998 | Grabenkort | |
| 5,779,677 A | 7/1998 | Frezza | |
| 5,807,334 A | 9/1998 | Hodosh et al. | |
| 5,817,058 A | 10/1998 | Shaw | |
| 5,827,262 A | 10/1998 | Neftel et al. | |
| 5,843,036 A | 12/1998 | Olive et al. | |
| 5,855,839 A | 1/1999 | Brunel | |
| 5,865,795 A | 2/1999 | Schiff et al. | |
| 5,865,804 A | 2/1999 | Bachynsky | |
| 5,868,711 A | 2/1999 | Kramer et al. | |
| 5,879,327 A | 3/1999 | Moreau DeFarges et al. | |
| 5,913,843 A | 6/1999 | Jentzen | |
| 5,928,205 A | 7/1999 | Marshall | |
| 5,954,738 A | 9/1999 | LeVaughn et al. | |
| 5,957,897 A | 9/1999 | Jeffrey | |
| 5,960,797 A | 10/1999 | Kramer et al. | |
| 5,997,513 A | 12/1999 | Smith et al. | |
| 6,007,515 A | 12/1999 | Epstein et al. | |
| 6,015,438 A | 1/2000 | Shaw | |
| 6,017,330 A | 1/2000 | Hitchins et al. | |
| 6,036,675 A | 3/2000 | Thorne et al. | |
| 6,045,534 A | 4/2000 | Jacobsen et al. | |
| 6,068,614 A | 5/2000 | Kimber et al. | |
| 6,077,247 A | 6/2000 | Marshall et al. | |
| 6,083,197 A | 7/2000 | Umbaugh | |
| 6,086,562 A | 7/2000 | Jacobsen et al. | |
| 6,090,070 A | 7/2000 | Hager et al. | |
| 6,090,078 A | 7/2000 | Erskine | |
| 6,090,897 A | 7/2000 | Akasaki et al. | |
| 6,099,503 A | 8/2000 | Stradella | |
| 6,099,504 A | 8/2000 | Gross | |
| 6,123,684 A | 9/2000 | Deboer et al. | |
| 6,139,534 A * | 10/2000 | Niedospial et al. | 604/411 |
| 6,159,161 A | 12/2000 | Hodosh | |
| 6,159,181 A | 12/2000 | Crossman et al. | |
| 6,159,184 A | 12/2000 | Perez et al. | |
| 6,162,199 A | 12/2000 | Geringer | |
| 6,171,276 B1 | 1/2001 | Lippe et al. | |
| 6,179,812 B1 | 1/2001 | Botich et al. | |
| 6,186,980 B1 | 2/2001 | Brunel | |
| 6,190,363 B1 | 2/2001 | Gabbard et al. | |
| 6,193,696 B1 | 2/2001 | Jansen et al. | |
| 6,203,530 B1 | 3/2001 | Stewart, Sr. | |
| 6,209,738 B1 | 4/2001 | Jansen et al. | |
| 6,221,044 B1 | 4/2001 | Greco | |
| 6,258,068 B1 | 7/2001 | Kirchhofer et al. | |
| 6,270,479 B1 | 8/2001 | Bergens et al. | |
| 6,280,421 B1 | 8/2001 | Kirchhofer et al. | |
| 6,290,683 B1 | 9/2001 | Erez et al. | |
| 6,293,925 B1 | 9/2001 | Safabash et al. | |
| 6,317,939 B1 | 11/2001 | Malin | |
| 6,330,960 B1 | 12/2001 | Faughey et al. | |

(56) References Cited

U.S. PATENT DOCUMENTS

| | | |
|---|---|---|
| 6,332,875 B2 | 12/2001 | Inkpen et al. |
| 6,371,939 B2 | 4/2002 | Bergens et al. |
| 6,371,959 B1 | 4/2002 | Trice |
| 6,387,078 B1 | 5/2002 | Gillespie, III |
| 6,391,003 B1 | 5/2002 | Lesch, Jr. |
| 6,419,658 B1 | 7/2002 | Restelli et al. |
| 6,428,528 B2 | 8/2002 | Sadowski et al. |
| 6,447,480 B1 | 9/2002 | Brunel |
| 6,454,743 B1 | 9/2002 | Weber |
| 6,454,746 B1 | 9/2002 | Bydion et al. |
| 6,461,333 B1 | 10/2002 | Frezza |
| 6,491,667 B1 | 12/2002 | Keane et al. |
| 6,517,517 B1 | 2/2003 | Farrugia et al. |
| 6,537,252 B1 | 3/2003 | Hansen |
| 6,544,234 B1 | 4/2003 | Gabriel |
| 6,565,540 B1 | 5/2003 | Perouse et al. |
| 6,565,553 B2 | 5/2003 | Sadowski et al. |
| 6,569,115 B1 | 5/2003 | Barker et al. |
| 6,569,123 B2 | 5/2003 | Aichas et al. |
| 6,569,124 B1 | 5/2003 | Perouse |
| 6,572,581 B1 | 6/2003 | Landau |
| 6,575,939 B1 | 6/2003 | Brunel |
| 6,585,702 B1 | 7/2003 | Brunel |
| 6,589,210 B1 | 7/2003 | Rolfe |
| 6,595,957 B1 | 7/2003 | Griffiths et al. |
| 6,595,962 B1 | 7/2003 | Perthu |
| 6,599,272 B1 | 7/2003 | Hjertman et al. |
| 6,607,508 B2 | 8/2003 | Knauer |
| 6,607,510 B2 | 8/2003 | Landau |
| 6,613,022 B1 | 9/2003 | Doyle |
| 6,620,137 B2 | 9/2003 | Kirchhofer et al. |
| 6,638,256 B2 | 10/2003 | Jansen et al. |
| 6,641,554 B2 | 11/2003 | Landau |
| 6,641,560 B1 | 11/2003 | Bechtold et al. |
| 6,641,565 B1 | 11/2003 | Lavi et al. |
| 6,645,170 B2 | 11/2003 | Landau |
| 6,645,181 B1 | 11/2003 | Lavi et al. |
| 6,648,835 B1 | 11/2003 | Shemesh |
| 6,648,850 B2 | 11/2003 | Landau |
| 6,656,163 B1 | 12/2003 | Marshall et al. |
| 6,673,049 B2 | 1/2004 | Hommann et al. |
| 6,676,630 B2 | 1/2004 | Landau et al. |
| 6,689,093 B2 | 2/2004 | Landau et al. |
| 6,692,469 B1 | 2/2004 | Weekes et al. |
| 6,699,220 B1 | 3/2004 | Rolfe |
| 6,740,062 B2 | 5/2004 | Hjertman |
| 6,743,199 B2 | 6/2004 | Shue et al. |
| 6,743,203 B1 | 6/2004 | Pickhard et al. |
| 6,746,429 B2 | 6/2004 | Sadowski et al. |
| 6,767,336 B1 | 7/2004 | Kaplan |
| 6,770,056 B2 | 8/2004 | Price et al. |
| 6,776,777 B2 | 8/2004 | Barelle |
| 6,783,509 B1 | 8/2004 | Landau et al. |
| 6,793,161 B1 | 9/2004 | Fujia et al. |
| 6,796,967 B2 | 9/2004 | Jensen |
| 6,811,548 B2 | 11/2004 | Jeffrey |
| 6,846,303 B2 | 1/2005 | Eakins et al. |
| 6,890,319 B1 | 5/2005 | Crocker |
| 6,899,698 B2 | 5/2005 | Sams |
| 6,932,793 B1 | 8/2005 | Marshall et al. |
| 6,939,319 B1 | 9/2005 | Anstead et al. |
| 6,979,316 B1 | 12/2005 | Rubin et al. |
| 7,066,907 B2 | 6/2006 | Crossman et al. |
| 7,097,634 B2 | 8/2006 | Gilbert |
| 7,118,553 B2 | 10/2006 | Scherer |
| 7,156,823 B2 | 1/2007 | Landau et al. |
| 7,160,913 B2 | 1/2007 | Schneider |
| 7,294,122 B2 | 11/2007 | Kubo et al. |
| 7,354,427 B2* | 4/2008 | Fangrow ................. 604/413 |
| RE40,428 E | 7/2008 | Keane et al. |
| 7,442,185 B2 | 10/2008 | Amark et al. |
| 7,470,258 B2 | 12/2008 | Barker et al. |
| 7,507,227 B2* | 3/2009 | Fangrow ................. 604/414 |
| 7,510,547 B2* | 3/2009 | Fangrow ................. 604/414 |
| 7,510,548 B2* | 3/2009 | Fangrow ................. 604/415 |
| 7,513,895 B2* | 4/2009 | Fangrow ................. 604/414 |
| 7,534,238 B2* | 5/2009 | Fangrow ................. 604/414 |
| 7,547,300 B2* | 6/2009 | Fangrow ................. 604/411 |
| 7,618,396 B2 | 11/2009 | Slate et al. |
| 7,635,356 B2 | 12/2009 | Stamp |
| 7,645,271 B2* | 1/2010 | Fangrow ................. 604/414 |
| 7,654,995 B2* | 2/2010 | Warren et al. ............. 604/414 |
| 7,658,733 B2* | 2/2010 | Fangrow ................. 604/415 |
| 7,682,345 B2 | 3/2010 | Savage |
| 7,717,879 B2 | 5/2010 | Mansouri |
| 7,744,561 B2 | 6/2010 | Stamp |
| 7,759,654 B2 | 7/2010 | Yan et al. |
| 7,794,434 B2 | 9/2010 | Mounce et al. |
| 7,811,262 B2 | 10/2010 | Moberg et al. |
| 7,828,764 B2 | 11/2010 | Moberg et al. |
| 7,871,397 B2 | 1/2011 | Schraga |
| 7,879,010 B2 | 2/2011 | Hunn et al. |
| 7,959,715 B2 | 6/2011 | Kavazov et al. |
| 7,976,499 B2 | 7/2011 | Grunhut et al. |
| 8,100,154 B2 | 1/2012 | Reynolds et al. |
| 8,177,768 B2 | 5/2012 | Leinsing |
| 8,277,414 B2 | 10/2012 | Barrow-Williams et al. |
| 8,313,463 B2 | 11/2012 | Barrow-Williams et al. |
| 8,409,138 B2 | 4/2013 | James et al. |
| 8,491,530 B2 | 7/2013 | Maritan |
| 8,696,628 B2 | 4/2014 | Grunhut |
| 2001/0005781 A1 | 6/2001 | Bergens et al. |
| 2001/0021828 A1 | 9/2001 | Fischer et al. |
| 2001/0037087 A1 | 11/2001 | Knauer |
| 2001/0037089 A1 | 11/2001 | Domici, Jr. |
| 2001/0049496 A1 | 12/2001 | Kirchhofer et al. |
| 2001/0051789 A1 | 12/2001 | Parsons |
| 2002/0032412 A1 | 3/2002 | Riemelmoser |
| 2002/0072709 A1 | 6/2002 | Sadowski et al. |
| 2002/0095120 A1 | 7/2002 | Larsen et al. |
| 2002/0151839 A1 | 10/2002 | Landau |
| 2002/0161334 A1 | 10/2002 | Castellano et al. |
| 2002/0165500 A1 | 11/2002 | Bechtold et al. |
| 2002/0173752 A1 | 11/2002 | Polzin |
| 2002/0183690 A1 | 12/2002 | Arnisolle |
| 2003/0036679 A1 | 2/2003 | Kortenbach |
| 2003/0036725 A1 | 2/2003 | Lavi et al. |
| 2003/0050609 A1 | 3/2003 | Sams |
| 2003/0060773 A1 | 3/2003 | Nguyen |
| 2003/0065286 A1 | 4/2003 | Landau |
| 2003/0078546 A1 | 4/2003 | Jensen |
| 2003/0088207 A1 | 5/2003 | Rogatchev et al. |
| 2003/0088216 A1 | 5/2003 | Py |
| 2003/0093030 A1 | 5/2003 | Landau |
| 2003/0093035 A1 | 5/2003 | Mohammed |
| 2003/0093036 A1 | 5/2003 | Crossman et al. |
| 2003/0105430 A1 | 6/2003 | Lavi et al. |
| 2003/0109833 A1 | 6/2003 | Sharpe |
| 2003/0120212 A1 | 6/2003 | Dedig et al. |
| 2003/0120222 A1 | 6/2003 | Vaillancourt |
| 2003/0121815 A1 | 7/2003 | Bergeron et al. |
| 2003/0135157 A1 | 7/2003 | Saulenas et al. |
| 2003/0181859 A1 | 9/2003 | Brunel |
| 2003/0184973 A1 | 10/2003 | Nagata et al. |
| 2003/0196928 A1 | 10/2003 | Parsons |
| 2003/0199814 A1 | 10/2003 | Parsons et al. |
| 2003/0208164 A1 | 11/2003 | Botich et al. |
| 2003/0212362 A1 | 11/2003 | Roser |
| 2003/0212370 A1 | 11/2003 | Barrelle |
| 2003/0212380 A1 | 11/2003 | Barrelle |
| 2003/0225368 A1 | 12/2003 | Landau et al. |
| 2003/0229308 A1 | 12/2003 | Tsals et al. |
| 2003/0233070 A1 | 12/2003 | De La serna et al. |
| 2003/0236502 A1 | 12/2003 | De La Serna et al. |
| 2003/0236504 A1 | 12/2003 | Chen |
| 2004/0002684 A1* | 1/2004 | Lopez ................. 604/240 |
| 2004/0015134 A1 | 1/2004 | Lavi et al. |
| 2004/0019326 A1 | 1/2004 | Gilbert et al. |
| 2004/0024367 A1 | 2/2004 | Gilbert |
| 2004/0039336 A1 | 2/2004 | Amark et al. |
| 2004/0039366 A1 | 2/2004 | MacLeod |
| 2004/0069044 A1 | 4/2004 | Lavi et al. |
| 2004/0087897 A1 | 5/2004 | Hjertman |
| 2004/0102740 A1 | 5/2004 | Meloul |

(56) References Cited

U.S. PATENT DOCUMENTS

| | | |
|---|---|---|
| 2004/0111054 A1 | 6/2004 | Landau et al. |
| 2004/0111057 A1 | 6/2004 | Wilkinson |
| 2004/0133159 A1 | 7/2004 | Haider et al. |
| 2004/0138618 A1 | 7/2004 | Mazzoni |
| 2004/0143224 A1 | 7/2004 | Field et al. |
| 2004/0153033 A1 | 8/2004 | Mazzoni |
| 2004/0225262 A1 | 11/2004 | Fathallah et al. |
| 2004/0243065 A1 | 12/2004 | McConnell et al. |
| 2005/0011780 A1 | 1/2005 | Simon et al. |
| 2005/0020979 A1 | 1/2005 | Westbye et al. |
| 2005/0020980 A1 | 1/2005 | Inoue et al. |
| 2005/0027255 A1 | 2/2005 | Lavi et al. |
| 2005/0033234 A1 | 2/2005 | Sadowski et al. |
| 2005/0035029 A1 | 2/2005 | Grob |
| 2005/0040716 A1 | 2/2005 | Schmid et al. |
| 2005/0049550 A1 | 3/2005 | Kirchhofer et al. |
| 2005/0049561 A1 | 3/2005 | Hommann et al. |
| 2005/0075608 A1 | 4/2005 | Holdgate et al. |
| 2005/0085776 A1 | 4/2005 | Hommann et al. |
| 2005/0090782 A1 | 4/2005 | Marshall et al. |
| 2005/0097238 A1 | 5/2005 | Oomori et al. |
| 2005/0101919 A1 | 5/2005 | Brunnberg |
| 2005/0124940 A1 | 6/2005 | Martin et al. |
| 2005/0125019 A1 | 6/2005 | Kudna et al. |
| 2005/0137523 A1 | 6/2005 | Wyatt et al. |
| 2005/0168855 A1 | 8/2005 | Fanelli et al. |
| 2005/0203466 A1 | 9/2005 | Hommann et al. |
| 2005/0209554 A1 | 9/2005 | Landau |
| 2005/0215941 A1 | 9/2005 | Bernard et al. |
| 2005/0215951 A1 | 9/2005 | Saulenas et al. |
| 2005/0222539 A1 | 10/2005 | Gonzales et al. |
| 2005/0261633 A1 | 11/2005 | Khalaj |
| 2005/0261634 A1 | 11/2005 | Karlsson |
| 2005/0267403 A1 | 12/2005 | Landau et al. |
| 2005/0273054 A1 | 12/2005 | Asch |
| 2005/0273055 A1 | 12/2005 | Harrison et al. |
| 2005/0277885 A1 | 12/2005 | Scherer |
| 2005/0277886 A1 | 12/2005 | Hommann et al. |
| 2005/0277896 A1 | 12/2005 | Messerli et al. |
| 2005/0288633 A1 | 12/2005 | Jeffrey |
| 2006/0016835 A1 | 1/2006 | Perry |
| 2006/0030819 A1 | 2/2006 | Young et al. |
| 2006/0036216 A1 | 2/2006 | Rimlinger et al. |
| 2006/0036217 A1 | 2/2006 | Doyle |
| 2006/0069345 A1 | 3/2006 | Anderson et al. |
| 2006/0069348 A1 | 3/2006 | Parker et al. |
| 2006/0069350 A1 | 3/2006 | Buenger et al. |
| 2006/0079834 A1 | 4/2006 | Tennican et al. |
| 2006/0100588 A1 | 5/2006 | Brunnberg et al. |
| 2006/0106295 A1 | 5/2006 | Jais et al. |
| 2006/0161111 A1 | 7/2006 | Potter et al. |
| 2006/0178631 A1 | 8/2006 | Gillespie et al. |
| 2006/0178642 A1 | 8/2006 | Gillespie et al. |
| 2006/0184119 A1 | 8/2006 | Remde et al. |
| 2006/0184137 A1 | 8/2006 | Reynolds |
| 2006/0189938 A1 | 8/2006 | Hommann et al. |
| 2006/0200093 A1 | 9/2006 | Lopez |
| 2006/0206060 A1 | 9/2006 | Lopez |
| 2006/0224124 A1 | 10/2006 | Scherer |
| 2006/0229572 A1 | 10/2006 | Lopez |
| 2006/0258986 A1 | 11/2006 | Hunter et al. |
| 2006/0258990 A1 | 11/2006 | Weber |
| 2006/0270986 A1 | 11/2006 | Hommann et al. |
| 2007/0027430 A1 | 2/2007 | Hommann |
| 2007/0032775 A1* | 2/2007 | Niedospial et al. ............ 604/415 |
| 2007/0066939 A1 | 3/2007 | Krulevitch et al. |
| 2007/0078382 A1 | 4/2007 | Hommann et al. |
| 2007/0078428 A1* | 4/2007 | Reynolds et al. ............. 604/411 |
| 2007/0118094 A1 | 5/2007 | Bingham et al. |
| 2007/0142787 A1 | 6/2007 | Scherer |
| 2007/0156091 A1* | 7/2007 | Fathallah et al. ............. 604/151 |
| 2007/0156112 A1 | 7/2007 | Walsh |
| 2007/0208296 A1 | 9/2007 | Paproski et al. |
| 2007/0244456 A1* | 10/2007 | Fangrow ........................ 604/411 |
| 2007/0244457 A1* | 10/2007 | Fangrow ........................ 604/411 |
| 2007/0244458 A1* | 10/2007 | Fangrow ........................ 604/411 |
| 2007/0244459 A1* | 10/2007 | Fangrow ........................ 604/411 |
| 2007/0244460 A1* | 10/2007 | Fangrow ........................ 604/411 |
| 2007/0244461 A1* | 10/2007 | Fangrow ........................ 604/411 |
| 2007/0244462 A1* | 10/2007 | Fangrow ........................ 604/411 |
| 2007/0244463 A1* | 10/2007 | Warren et al. ................. 604/411 |
| 2007/0244464 A1* | 10/2007 | Fangrow et al. .............. 604/411 |
| 2007/0244465 A1* | 10/2007 | Fangrow ........................ 604/411 |
| 2007/0244466 A1* | 10/2007 | Fangrow ........................ 604/411 |
| 2008/0033395 A1 | 2/2008 | Alchas |
| 2008/0161770 A1* | 7/2008 | Fangrow ........................ 604/411 |
| 2008/0172024 A1* | 7/2008 | Yow ................................ 604/411 |
| 2008/0213590 A1 | 9/2008 | Greiner et al. |
| 2008/0249498 A1* | 10/2008 | Fangrow ........................ 604/411 |
| 2008/0269680 A1 | 10/2008 | Ibranyan et al. |
| 2008/0306443 A1 | 12/2008 | Neer et al. |
| 2008/0312602 A1 | 12/2008 | Barrow-Williams et al. |
| 2008/0312606 A1 | 12/2008 | Harrison et al. |
| 2009/0036764 A1 | 2/2009 | Rivas et al. |
| 2009/0054849 A1 | 2/2009 | Burnell et al. |
| 2009/0088688 A1 | 4/2009 | Timothy Donald et al. |
| 2009/0209554 A1 | 8/2009 | Boyd et al. |
| 2009/0234297 A1 | 9/2009 | Jennings |
| 2010/0016793 A1 | 1/2010 | Jennings et al. |
| 2010/0036319 A1 | 2/2010 | Drake et al. |
| 2011/0092954 A1 | 4/2011 | Jennings |
| 2011/0098647 A1 | 4/2011 | Jennings |
| 2011/0098655 A1 | 4/2011 | Jennings et al. |
| 2011/0130743 A1 | 6/2011 | Jennings et al. |
| 2011/0282278 A1 | 11/2011 | Stamp et al. |
| 2012/0232491 A1 | 9/2012 | Jennings |
| 2012/0323177 A1 | 12/2012 | Adams et al. |
| 2013/0096512 A1 | 4/2013 | Ekman et al. |
| 2013/0267898 A1 | 10/2013 | Hourmand et al. |
| 2013/0317446 A1 | 11/2013 | Hourmand et al. |
| 2013/0331794 A1 | 12/2013 | Ekman et al. |
| 2013/0338601 A1 | 12/2013 | Cowe |
| 2013/0345643 A1 | 12/2013 | Hourmand et al. |

FOREIGN PATENT DOCUMENTS

| | | |
|---|---|---|
| CN | 1190599 A | 8/1998 |
| CN | 1420794 A | 5/2003 |
| CN | 1541121 A | 10/2004 |
| CN | 1550240 A | 12/2004 |
| CN | 101014379 A | 8/2007 |
| CN | 101068585 A | 11/2007 |
| DE | 902776 C | 1/1954 |
| DE | 3604826 A1 | 10/1986 |
| DE | 4428467 A1 | 2/1996 |
| DE | 19603707 A1 | 8/1997 |
| DE | 69506521 T2 | 6/1999 |
| DE | 10137962 A1 | 2/2003 |
| DE | 10207276 A1 | 9/2003 |
| EP | 0111724 B1 | 11/1983 |
| EP | 0096314 A2 | 12/1983 |
| EP | 0144625 A2 | 6/1985 |
| EP | 0240787 A2 | 3/1987 |
| EP | 0515473 B1 | 12/1992 |
| EP | 0518416 A1 | 12/1992 |
| EP | 0331452 A2 | 8/1993 |
| EP | 0585626 A1 | 3/1994 |
| EP | 0389938 B1 | 5/1994 |
| EP | 0516473 B1 | 2/1996 |
| EP | 0482677 B1 | 4/1998 |
| EP | 0602883 B1 | 7/1998 |
| EP | 0857491 A1 | 8/1998 |
| EP | 0824922 B1 | 4/2002 |
| EP | 1260241 A1 | 11/2002 |
| EP | 0824923 B1 | 7/2003 |
| EP | 1228777 B1 | 10/2003 |
| EP | 0991441 B1 | 12/2003 |
| EP | 1166809 B1 | 3/2004 |
| EP | 0666084 B1 | 4/2004 |
| EP | 0941133 B1 | 4/2004 |
| EP | 1124601 B1 | 12/2004 |
| EP | 1364667 B1 | 4/2005 |
| EP | 1208858 B1 | 6/2006 |
| EP | 1755710 A1 | 2/2007 |

(56) References Cited

FOREIGN PATENT DOCUMENTS

| | | |
|---|---|---|
| EP | 1586341 B1 | 1/2008 |
| EP | 1932558 A1 | 6/2008 |
| EP | 2023980 A1 | 2/2009 |
| EP | 2129414 A1 | 12/2009 |
| EP | 1755706 B1 | 3/2010 |
| EP | 1928523 B1 | 7/2010 |
| EP | 1518575 B1 | 11/2010 |
| EP | 2468330 A1 | 6/2012 |
| FR | 1169935 A | 1/1959 |
| FR | 1538565 A | 9/1968 |
| FR | 2629706 A | 10/1989 |
| FR | 2654938 A1 | 5/1991 |
| FR | 2665079 A1 | 1/1992 |
| FR | 2717086 A1 | 9/1995 |
| FR | 2741810 A1 | 6/1997 |
| FR | 2805868 A1 | 9/2001 |
| FR | 2830765 A1 | 4/2003 |
| FR | 2861310 A1 | 4/2005 |
| GB | 143084 | 5/1920 |
| GB | 0412054 | 6/1934 |
| GB | 728248 | 4/1955 |
| GB | 909898 | 11/1962 |
| GB | 1263355 | 2/1972 |
| GB | 1311937 A | 3/1973 |
| GB | 1514725 | 6/1978 |
| GB | 2338033 A | 12/1999 |
| GB | 2388033 A | 11/2003 |
| GB | 2396298 A | 6/2004 |
| GB | 2396816 A | 7/2004 |
| GB | 2397767 A | 8/2004 |
| GB | 2404338 A | 2/2005 |
| GB | 2414398 A | 11/2005 |
| GB | 2414399 A | 11/2005 |
| GB | 2414400 A | 11/2005 |
| GB | 2414401 A | 11/2005 |
| GB | 2414402 A | 11/2005 |
| GB | 2414403 A | 11/2005 |
| GB | 2424835 A | 10/2006 |
| GB | 2424836 A | 10/2006 |
| GB | 2424838 A | 10/2006 |
| GB | 2433035 A | 6/2007 |
| GB | 2437922 A | 11/2007 |
| GB | 2438591 A | 12/2007 |
| GB | 2443606 A | 5/2008 |
| GB | 2445090 A | 6/2008 |
| GB | 2446778 A | 8/2008 |
| GB | 2451663 A | 2/2009 |
| GB | 2451665 A | 2/2009 |
| GB | 2452286 A | 3/2009 |
| JP | 2-185261 A | 7/1990 |
| JP | 2-502971 T | 9/1990 |
| JP | 02-299660 A | 12/1990 |
| JP | 11-501549 T | 2/1992 |
| JP | 5-161712 A | 6/1993 |
| JP | 6-209996 A | 8/1994 |
| JP | 6-327770 A | 11/1994 |
| JP | 07-116224 A | 5/1995 |
| JP | 7-213610 A | 8/1995 |
| JP | 7-222799 A | 8/1995 |
| JP | 8-502180 T | 3/1996 |
| JP | 8-504354 T | 5/1996 |
| JP | 9-225029 A | 9/1997 |
| JP | 10-504474 T | 5/1998 |
| JP | 10-507935 A | 8/1998 |
| JP | 11-503637 T | 3/1999 |
| JP | 11-504536 T | 4/1999 |
| JP | 11-164887 T | 6/1999 |
| JP | 11-512332 T | 10/1999 |
| JP | 2000-126293 A | 5/2000 |
| JP | 2000-510021 T | 8/2000 |
| JP | 2001-046498 A | 2/2001 |
| JP | 2001-212237 A | 8/2001 |
| JP | 2002-500933 T | 1/2002 |
| JP | 2002-502296 A | 1/2002 |
| JP | 2002-095749 A | 4/2002 |
| JP | 2002-513547 T | 5/2002 |
| JP | 2002-526175 A | 8/2002 |
| JP | 2002-528182 T | 9/2002 |
| JP | 2003-511105 T | 3/2003 |
| JP | 2003-532500 T | 11/2003 |
| JP | 2003-533288 A | 11/2003 |
| JP | 2004-533282 T | 11/2004 |
| JP | 2004-537376 T | 12/2004 |
| JP | 2005-508214 A | 3/2005 |
| JP | 2005-177503 A | 7/2005 |
| JP | 2004-33737 A | 8/2005 |
| JP | 2006-223858 A | 8/2006 |
| JP | 2008-284177 A | 11/2008 |
| NZ | 335985 A | 4/2001 |
| NZ | 573171 A | 11/2010 |
| NZ | 573350 A | 12/2010 |
| WO | WO 88/10129 A1 | 12/1988 |
| WO | WO 98/10129 A1 | 12/1988 |
| WO | WO 92/19296 A | 11/1992 |
| WO | WO 93/02186 A1 | 2/1993 |
| WO | WO 93/21986 A2 | 11/1993 |
| WO | WO 93/23098 A1 | 11/1993 |
| WO | WO 94/04207 A1 | 3/1994 |
| WO | WO 94/07554 A1 | 4/1994 |
| WO | WO 94/11041 | 5/1994 |
| WO | WO 94/13342 A1 | 6/1994 |
| WO | WO 94/21316 A1 | 9/1994 |
| WO | WO 94/22511 A1 | 10/1994 |
| WO | WO 95/04562 A1 | 2/1995 |
| WO | WO 95/29720 A1 | 11/1995 |
| WO | WO 95/31235 A1 | 11/1995 |
| WO | WO 95/35126 A1 | 11/1995 |
| WO | WO 95/35126 A1 | 12/1995 |
| WO | WO 96/30065 A1 | 10/1996 |
| WO | WO 97/10865 A1 | 3/1997 |
| WO | WO 97/13538 A1 | 4/1997 |
| WO | WO 97/48430 A1 | 12/1997 |
| WO | WO 98/11927 A1 | 3/1998 |
| WO | WO 99/03529 A2 | 1/1999 |
| WO | WO 99/10030 A2 | 3/1999 |
| WO | WO 99/22789 A1 | 5/1999 |
| WO | WO 99/37343 A | 7/1999 |
| WO | WO 99/53979 A1 | 10/1999 |
| WO | WO 99/59658 A1 | 11/1999 |
| WO | WO 00/06227 A1 | 2/2000 |
| WO | WO 00/07539 A1 | 2/2000 |
| WO | WO 00/13723 A2 | 3/2000 |
| WO | WO 00/24441 A1 | 5/2000 |
| WO | WO 00/35516 | 6/2000 |
| WO | WO 00/50107 A1 | 8/2000 |
| WO | WO 00/61209 A1 | 10/2000 |
| WO | WO 00/64515 A1 | 11/2000 |
| WO | WO 00/69488 A2 | 11/2000 |
| WO | WO 01/05456 A1 | 1/2001 |
| WO | WO 01/49347 A1 | 7/2001 |
| WO | WO 01/60435 A1 | 8/2001 |
| WO | WO 01/76666 A1 | 10/2001 |
| WO | WO 01/77384 A2 | 10/2001 |
| WO | WO 01/87384 A1 | 11/2001 |
| WO | WO 02/11799 A1 | 2/2002 |
| WO | WO 02/47746 A1 | 6/2002 |
| WO | WO 02/056947 A1 | 7/2002 |
| WO | WO 02/074361 A2 | 9/2002 |
| WO | 03/015846 | 2/2003 |
| WO | WO 03/013632 A2 | 2/2003 |
| WO | WO 03/015853 A1 | 2/2003 |
| WO | WO 03/039633 A2 | 5/2003 |
| WO | WO 03/041768 A | 5/2003 |
| WO | WO 03/047663 A2 | 6/2003 |
| WO | WO 03/051434 A2 | 6/2003 |
| WO | WO 03/066141 A1 | 8/2003 |
| WO | WO 03/092771 | 11/2003 |
| WO | WO 03/097133 | 11/2003 |
| WO | WO 03/099358 A2 | 12/2003 |
| WO | WO 2004/007554 A1 | 1/2004 |
| WO | WO 2004/011065 A1 | 2/2004 |
| WO | WO 2004/030732 A2 | 4/2004 |
| WO | WO 2004/035117 A2 | 4/2004 |
| WO | WO 2004/047890 A1 | 6/2004 |

(56) References Cited

FOREIGN PATENT DOCUMENTS

| | | |
|---|---|---|
| WO | WO 2004/047891 A1 | 6/2004 |
| WO | WO 2004/047892 A | 6/2004 |
| WO | WO 2004/054644 A1 | 7/2004 |
| WO | WO 2004/054645 A3 | 7/2004 |
| WO | WO 2004/087242 A1 | 10/2004 |
| WO | WO 2004/101025 A2 | 11/2004 |
| WO | WO 2004/108194 A1 | 12/2004 |
| WO | WO 2005/004961 A1 | 1/2005 |
| WO | WO 2005/009515 A1 | 2/2005 |
| WO | WO 2005/023341 A1 | 3/2005 |
| WO | WO 2005/025636 A2 | 3/2005 |
| WO | WO 2005/030301 A1 | 4/2005 |
| WO | WO 2005/035028 A1 | 4/2005 |
| WO | WO 2005/044345 A | 5/2005 |
| WO | WO 2005/044347 A1 | 5/2005 |
| WO | 2005/058393 | 6/2005 |
| WO | WO 2005/058396 A1 | 6/2005 |
| WO | WO 2005/070481 A1 | 8/2005 |
| WO | WO 2005/082438 A1 | 9/2005 |
| WO | WO 2005/097238 A3 | 10/2005 |
| WO | WO 2005/105014 A2 | 11/2005 |
| WO | WO 2005/115507 A1 | 12/2005 |
| WO | WO 2005/115508 A1 | 12/2005 |
| WO | WO 2005/115509 A1 | 12/2005 |
| WO | WO 2005/115510 A1 | 12/2005 |
| WO | WO 2005/115512 A1 | 12/2005 |
| WO | WO 2005/115513 A1 | 12/2005 |
| WO | WO 2005/115514 A1 | 12/2005 |
| WO | WO 2005/115516 A1 | 12/2005 |
| WO | WO 2005/120607 A2 | 12/2005 |
| WO | WO 2006/008086 A1 | 1/2006 |
| WO | WO 2006/044236 A2 | 4/2006 |
| WO | WO 2006/050304 A1 | 5/2006 |
| WO | WO 2006/062788 A2 | 6/2006 |
| WO | WO 2006/063015 A2 | 6/2006 |
| WO | WO 2006/063124 A2 | 6/2006 |
| WO | WO 2006/088513 A1 | 8/2006 |
| WO | WO 2006/088630 A2 | 8/2006 |
| WO | WO 2006/099441 A2 | 9/2006 |
| WO | WO 2006/106290 A1 | 10/2006 |
| WO | WO 2006/106291 A1 | 10/2006 |
| WO | WO 2006/106292 A1 | 10/2006 |
| WO | WO 2006/106293 A1 | 10/2006 |
| WO | WO 2006/106294 A | 10/2006 |
| WO | WO 2006/106295 A1 | 10/2006 |
| WO | WO 2006/118616 A1 | 11/2006 |
| WO | WO 2006/129196 A1 | 12/2006 |
| WO | WO 2007/027204 A2 | 3/2007 |
| WO | WO 2007/036676 A1 | 4/2007 |
| WO | WO 2007/047200 A1 | 4/2007 |
| WO | WO 2007/051330 A1 | 5/2007 |
| WO | WO 2007/066152 A | 6/2007 |
| WO | 2007/129324 | 11/2007 |
| WO | WO 2007/122193 A1 | 11/2007 |
| WO | WO 2007/131013 A | 11/2007 |
| WO | WO 2007/138299 A1 | 12/2007 |
| WO | WO 2008/047372 A2 | 4/2008 |
| WO | WO 2008/075033 A | 6/2008 |
| WO | WO 2008/093063 A2 | 8/2008 |
| WO | WO 88/08725 | 11/2008 |
| WO | 2010/023303 | 3/2010 |

OTHER PUBLICATIONS

Austrian Search Report dated Jan. 22, 2006; Application No. 200608166-5.
Australian Search Report dated Dec. 11, 2007; Application No. 200608165-7.
International Search Report dated Jun. 27, 2006; International Application No. PCT/GB2006/001023.
International Search Report dated Feb. 27, 2007; International Application No. PCT/IB2006/002792.
Great Britain Search Report dated Nov. 12, 2007; Application No. GB0715457.8.
European Search Report dated Aug. 3, 2011; Application No. 11170040.
European Search Report dated Aug. 3, 2011; Application No. 11163779.9.
International Search Report dated Sep. 5, 2005; International Application No. PCT/GB2005/002117.
Singapore Search Report dated Mar. 15, 2012; Application No. SG 201007017-5.
International Search Report dated May 30, 2006; International Application No. PCT/GB2005/003725.
European Search Report dated Aug. 3, 2011; Application No. 11170040.7.
Australian Search Report dated Dec. 6, 2007; Application No. SG 200608164-0.
International Search Report dated Sep. 9, 2005; International Application No. PCT/GB2005/002126.
European Search Report dated Jul. 20, 2011; Application No. 11163762.5.
Austrian Search Report dated Nov. 5, 2008; Application No. 200608166-5.
International Search Report dated Sep. 5,2005; International Application No. PCT/GB2005/002131.
International Search Report dated Sep. 9, 2005; International Application No. PCT/GB2005/002120.
Australian Search Report dated Feb. 26, 2008; Application No. SG 200608071-7.
International Search Report dated Sep. 5, 2005; International Application No. PCT/GB2005/002137.
European Search Report dated Apr. 23, 2007; Application No. 06077332.2.
European Search Report dated Feb. 28, 2011; Application No. 10179733.0.
European Search Report dated Mar. 4, 2011; Application No. 10179736.3.
International Search Report dated Sep. 6, 2005; International Application No. PCT/GB2005/002108.
European Search Report dated Jun. 16, 2011; Application No. 11160134.0.
Singapore Search Report dated Feb. 26, 2008; Application No. 200608070-9.
International Search Report dated Sep. 5, 2005; International Application No. PCT/GB2005/002105.
International Search Report dated Sep. 5, 2005; International Application No. PCT/GB2005/002116.
Australian Search Report dated Dec. 5, 2007; International Application No. SG-200608165-7.
International Search Report dated Sep. 5, 2005; International Application No. PCT/GB2005/002128.
International Search Report dated May 23, 2006; International Application No. PCT/GB2006/001017.
European Search Report dated Apr. 17, 2012; International Application No. 12157660.7.
European Search Report dated Apr. 17, 2012; International Application No. 12157661.5.
European Search Report Dated Oct. 16, 2012; International Application No. 12177505.0.
International Search Report dated May 29, 2006; International Application No. PCT/GB2006/001018.
International Search Report dated Jun. 2, 2006; International Application No. PCT/GB2006/001030.
European Search Report dated Aug., 4, 2011; Application No. 11169691.0.
International Search Report dated Jun. 1, 2006; International Application No. PCT/GB2006/001029.
International Search Report dated Sep. 9, 2005 International Application No. PCT/GB2005/002135.
International Search Report dated May 30, 2006; International Application No. PCT/GB2006/001031.
International Search Report dated Oct. 9, 2007; International Application No. PCT/GB2006/001023.
European Search Report dated Feb. 1, 2006; Application No. 05255298.1.

(56) References Cited

OTHER PUBLICATIONS

International Search Report dated Feb. 27, 2007; International Application No. PCT/1B2006/002792.
Great Britain Search Report dated Sep. 22, 2006; Application No. GB0610860.9.
International Search Report dated Aug. 22, 2007; International Application No. PCT/GB2007/001992.
Great Britain Search Report dated Sep. 28, 2006; Application No. GB0610859.1.
International Search Report dated Sep. 4, 2007; International Application No. PCT/GB2007/002002.
International Search Report dated Aug. 22, 2007; International Application No. PCT/GB2007/001973.
International Search Report dated Feb. 26, 2008; International Application No. PCT/GB2007/004335.
Great Britain Search Report dated Sep. 29, 2006; Application No. GB0610856.7.
International Search Report dated Sep. 13, 2007; International Application No. PCT/GB2007/001999.
Great Britain Search Report dated Sep. 19, 2006; Application No. GB0610861.7.
International Search Report dated Aug. 28, 2007; International Application No. PCT/GB2007/001969.
Great Britain Search Report dated Nov. 12, 2007; Application No. GB0715460.2.
International Search Report dated Oct. 10, 2008; International Application No. PCT/GB2008/002578.
Great Britain Search Report dated Nov. 12, 2007; Application No. GB0715459.4.
International Search Report dated Oct. 14, 2008; International Application No. PCT/GB2008/002580.
Great Britain Search Report dated Nov. 12, 2007; Application No. GB0715461.0.
International Search Report dated Nov. 27, 2008; International Application No. PCT/GB2008/002579.
Great Britain Search Report dated Nov. 12, 2007; Application No. GB0715456.0.
International Search Report dated Oct. 10, 2008; International Application No. PCT/GB2008/002573.
Great Britain Search Report dated Nov. 8, 2007; Application No. GB0715457.8.
International Search Report dated Oct. 10, 2008; International Application No. PCT/GB2008/002583.
Great Britain Search Report dated Sep. 25, 2008; Application No. GB0811348.2.
International Search Report dated Sep. 30, 2009; International Application No. PCT/GB2009/001447.
European Search Report dated Oct. 15, 2013; Application No. 12182553.3.
Great Britain Search Report dated Sep. 25, 2008; Application No. GB0811346.6.
International Search Report dated Oct. 2, 2009; International Application No. PCT/GB2009/001448.
Great Britain Search Report dated Sep. 25, 2008; Application No. GB0811347.4.
International Search Report dated Oct. 5, 2009; International Application No. PCT/GB2009/001451.
Great Britain Search Report dated Sep. 25, 2008; Application No. GB0811345.8.
International Search Report dated Oct. 6, 2009; International Application No. PCT/GB2009/001453.
Great Britain Search Report dated Sep. 25, 2008; Application No. GB0811349.0.
International Search Report dated Oct. 5, 2009; International Application No. PCT/GB2009/001445.
Great Britain Search Report dated Sep. 25, 2008; Application No. GB0811343.3.
International Search Report dated Jan. 22, 2010; International Application No. PCT/GB2009/001446.
Great Britain Search Report dated Nov. 16, 2007; Application No. GB0716774.5.
International Search Report dated Jan. 12, 2008; International Application No. PCT/GB2008/002475.
Great Britain Search Report dated Dec. 9, 2013; Application No. GB1310394.0.
Great Britain Search Report dated Dec. 8, 2013; Application No. GB1310389.0.
Great Britain Search Report dated Dec. 9, 2013; Application No. GB1310402.1.
Great Britain Search Report dated Dec. 9, 2013; Application No. GB1310392.4.
Great Britain Search Report dated Dec. 10, 2013; Application No. GB1310393.2.
Great Britain Search Report dated Dec. 10, 2013; Application No. GB1310372.6.
International Search Report dated Sep. 8, 2014; International Application No. PCT/EP2014/062163.
International Search Report dated Sep. 8, 2014; International Application No. PCT/EP2014/062166.
International Search Report dated Sep. 17, 2014; International Application No. PCT/EP2014/062167.
International Search Report dated Sep. 9, 2014; International Application No. PCT/EP2014/062168.
International Search Report dated Sep. 8, 2014; International Application No. PCT/EP2014/062162.
International Search Report dated Sep. 16, 2014; International Application No. PCT/EP2014/062160.

\* cited by examiner

FIG. 3a
FIG. 3b
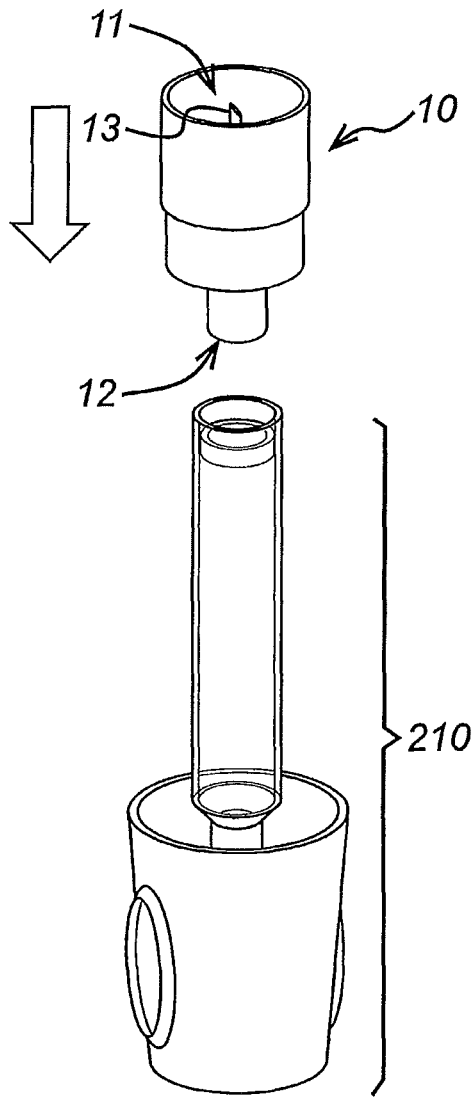
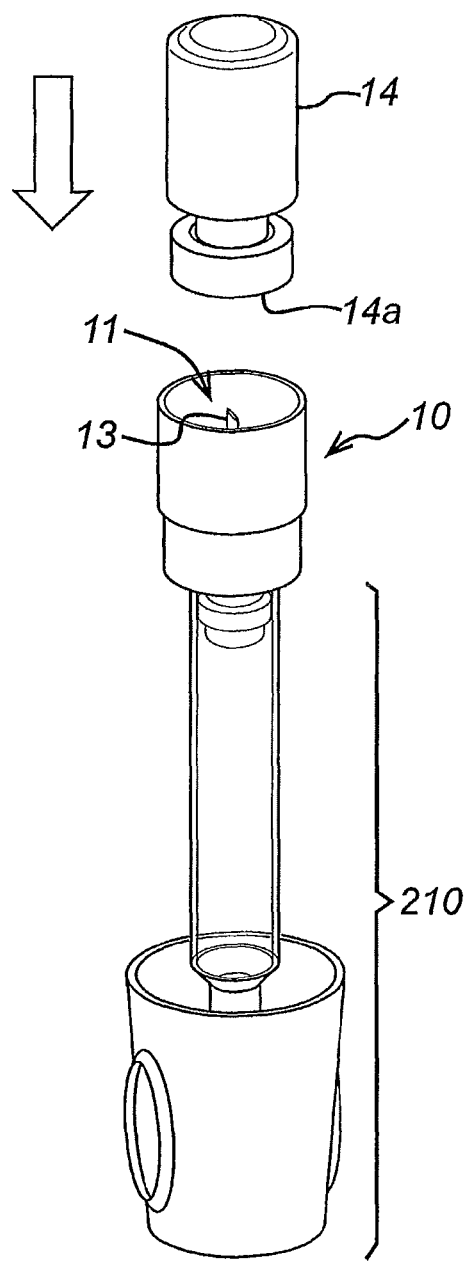

FLUID TRANSFER ASSEMBLY FOR A SYRINGE

FIELD OF THE INVENTION

The present invention relates to a fluid transfer assembly, a fluid transfer system, an injection kit comprising the fluid transfer system and a method of assembling an injection device.

BACKGROUND OF THE INVENTION

Subcutaneous drugs can be supplied to patients in a vial for home injection. The current method is for the patient to draw the drug from the vial into a syringe and perform a manual injection. The market is moving towards auto-injectors to carry out home injection. Auto-injectors which are manufactured and assembled including a pre-filled syringe of drug are known, for example from international patent application publication no. 2006/106295, which is incorporated herein by reference. There is currently no easy way for a patient to transfer a subcutaneous drug from a vial into an auto-injector.

SUMMARY OF THE INVENTION

The present invention aims to solve the aforementioned problems.

In a first aspect of the invention, there is provided a fluid transfer assembly having a means for connection to a syringe, means for receiving a vial having a closure element where the receiving means is adapted to engage and open the closure element and permit fluid to be transferred from the vial to the syringe.

This fluid transfer system can be used with a delivery device having a delivery sub-assembly and a reusable drive sub-assembly which are both adapted to be attached to the syringe and operate together to deliver fluid from the syringe. The fluid transfer assembly thus permits a conventional syringe to be used in conjunction with a vial and an injection device.

Preferably, the receiving means comprises a needle to pierce the closure element and extend into the vial. The needle may also form part of a fluid pathway which extends in use between the vial and the syringe. Thus, a fluid pathway between the syringe and vial can be readily achieved without substantial user intervention.

In one embodiment of the invention, the receiving means is a cylinder open at a first end which is dimensioned to receive the vial. Preferably, the connection means and receiving means are integrally formed with each other.

Advantageously, the connection means may comprise a second end which is open and dimensioned to fit over or in an open end of the syringe which is opposite the needle end of the syringe. This provides a stable, secure and sealed connection between the inside of the vial and the inside of the syringe.

Preferably, the fluid is transferred in use from the vial to the syringe under the force of gravity acting on the fluid, when the connection means is located above the receiving means. This means that limited input from a user of the injection device is required to fill the syringe and the transfer In a second aspect of the invention, there is provided a fluid transfer system comprising:
the fluid transfer assembly of any one of the preceding claims; and a syringe.

In a third aspect of the invention, there is provided an injection kit, comprising:

the fluid transfer system described above; and
a delivery device including a delivery sub-assembly and a drive sub-assembly, which are both adapted to be attached to the syringe, and operate together to deliver the fluid from the syringe.

Preferably, the delivery sub-assembly is adapted to support the syringe; and the drive sub-assembly comprises a drive adapted on activation to act on the syringe to advance it from a retracted position in which a discharge nozzle of the syringe is contained within the delivery sub-assembly to an extended position in which the discharge nozzle extends from the delivery sub-assembly.

In one embodiment of the invention, the delivery sub-assembly comprises: a syringe carrier adapted to support the syringe between its retracted and extended positions; and a retraction element adapted to move the syringe after fluid delivery from the extended position to the retracted position.

Preferably, the drive sub-assembly comprises a release mechanism to release the drive to act on the syringe to cause it to move from the retracted position to the extended position, wherein the drive is in a first position when the syringe is in its retracted position and the drive is in a second position when the syringe is in its extended position.

In one embodiment of the present invention, there is provided a base-station which is adapted to receive the drive sub-assembly and reset the drive by moving it from its second position to its first position and reset the release mechanism such that when actuated again it releases the drive. Preferably, the base station comprises an attachment to hold the delivery sub-assembly whilst it is being reset. The attachment may simply be a port, for example a cylindrical support that is dimensioned to surround the. The base-station may comprises a protrusion within the port which acts on the drive to force it into the housing, into its retracted position, when the injection device is inserted into the port.

Advantageously, the syringe may be disposable.

In a fourth aspect of the present invention, there is provided a method of assembling an injection device, comprising:
inserting fluid into a syringe through a vial via the fluid transfer assembly described above;
inserting a syringe having a piston into a delivery sub-assembly;
attaching a drive sub-assembly comprising a drive to the delivery sub-assembly; and
assembling the drive sub-assembly and delivery sub-assembly together.

The method may further comprise the step of resetting the drive assembly after activation of the drive. Advantageously, the transfer of the content of the vial to the syringe assembly can occur while the delivery assembly is on a base station.

BRIEF DESCRIPTION OF DRAWINGS

One or more embodiments of the present invention are described below with reference to the accompanying drawings, in which:

FIGS. 3a to 3c show perspective views of a fluid transfer assembly according to the present invention.

DETAILED DESCRIPTION OF THE DRAWINGS

Figure 1:
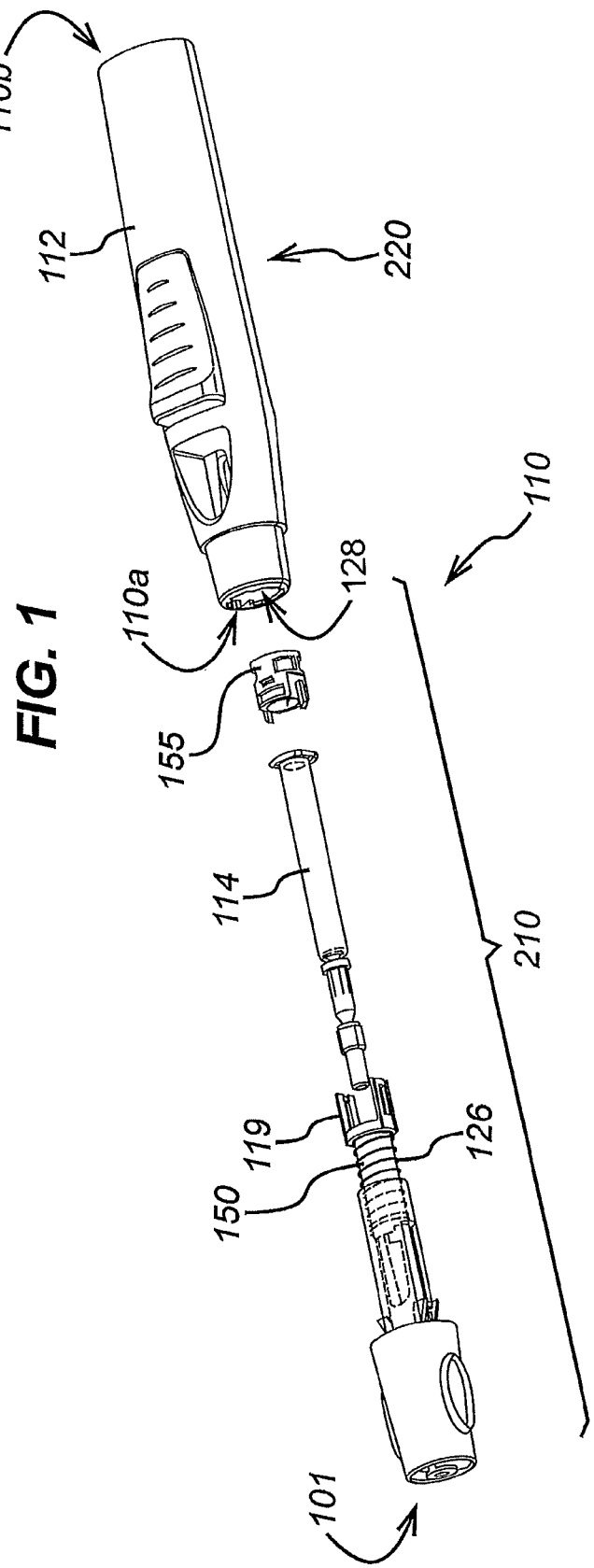
FIG. 1 shows a perspective view of sub-assemblies of the injection device according to the present invention.
Figure 2:
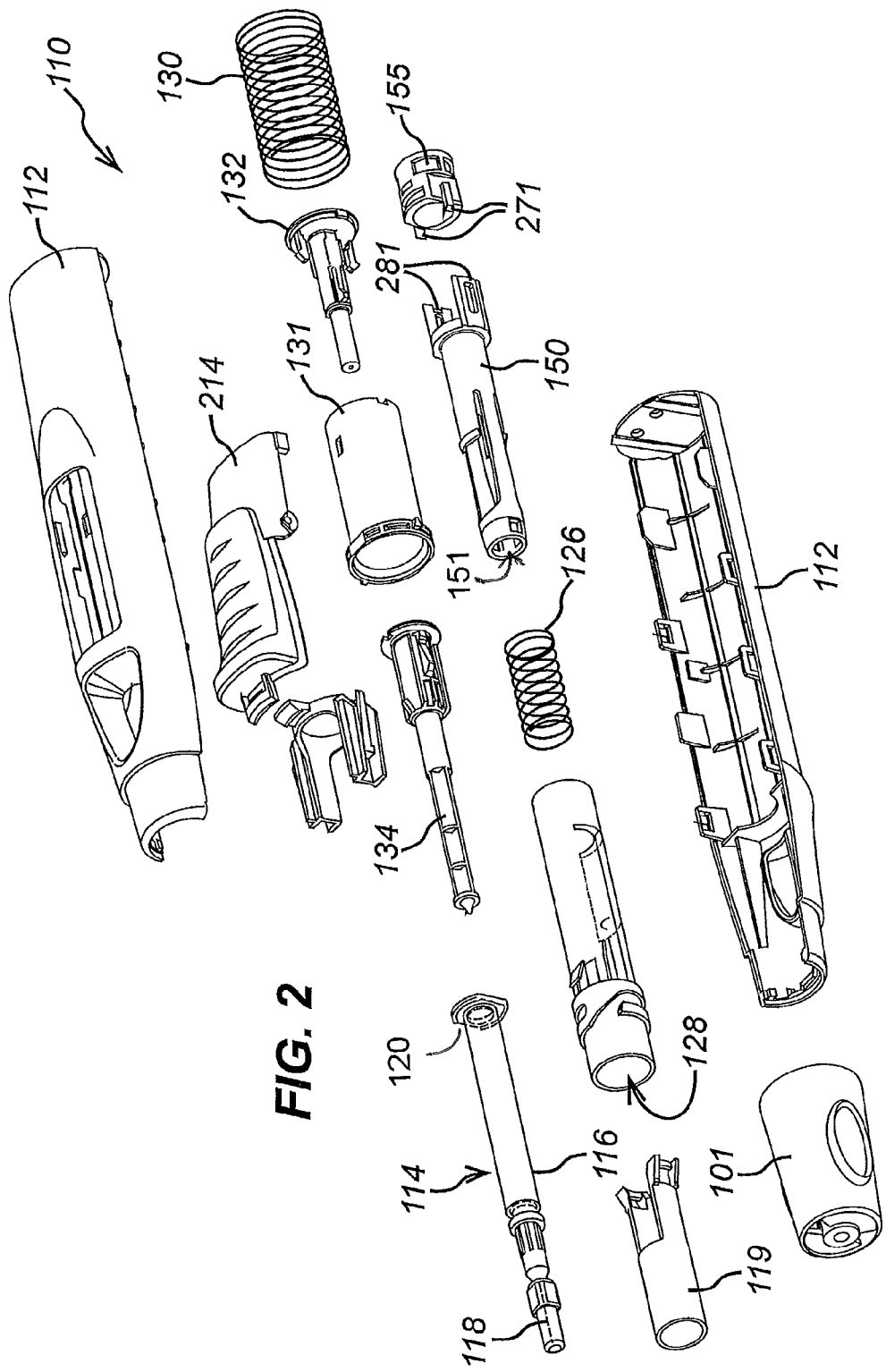
FIG. 2 shows an exploded view of components of the injection device according to the present invention.

FIGS. 1 and 2 show a delivery device 110 according to the present invention, having a delivery device housing 112 with a proximal end 110a and a distal end 110b. A distal end 110a of the housing 112 has an exit aperture 128, through which the end of a sleeve 119 can emerge.

The delivery device 110 is assembled from two sub-assemblies as shown in FIG. 1. A delivery sub-assembly 210 comprises a syringe carrier 150, an interchangeable release element 155, sleeve 119 and spring 126, as well as an end-cap 101.

A drive sub-assembly 220 comprises the housing 112 and drive elements and actuators of the injection device 110 as will be discussed below. Upon assembly of the two sub-assemblies 220, 210 to form the injection device 110, the drive assembly 220 is able to actuate the syringe 114 held by the delivery sub-assembly 210. After actuation, the two sub-assemblies can be separated and the drive elements and actuators of the drive assembly 220 reset for further use.

The housing 112 is adapted to receive a hypodermic syringe 114 of conventional type, including a syringe body 116 defining a reservoir and terminating at one end in a hypodermic needle 118 and at the other in a flange 120. The syringe body 116 is of substantially constant diameter along the length of the reservoir, and is of significantly smaller diameter close to the end of the syringe 114 which terminates in the hypodermic needle. A drive coupling 134 acts through the bung of the syringe 114 to discharge the contents of the syringe 114 through the needle 118. This drive coupling 134 constrains a drug to be administered within the reservoir defined by syringe body 116. Whilst the syringe 114 illustrated is of hypodermic type, this need not necessarily be so. Transcutaneous or ballistic dermal and subcutaneous syringes may also be used with the injection device of the present invention.

As illustrated, the syringe 114 is housed in the syringe carrier 150 within the delivery sub-assembly 210. The syringe carrier 150 has a proximal end 151 through which the needle 118 of the syringe protrudes. The return spring 126, via the return spring support and the syringe carrier 150 biases the syringe 114 from an extended position in which the needle 118 extends from the aperture 128 in the housing 112 to a retracted position in which the needle 118 is contained within the housing 112.

The syringe carrier 150 comprises a sheath (not shown) into which the syringe 114 can be inserted from a distal end. The syringe 114 is provided with a boot (not shown). If the syringe were to fail or break, the sheath, which surrounds the syringe 114 along its length, would contain the broken pieces of syringe and reduce the likelihood of them from escaping from the injection device 110.

The housing of the drive assembly also includes an actuator, and a drive which here takes the form of a compression drive spring 130. Drive from the drive spring 130 is transmitted via a multi-component drive to the piston of the syringe 114 to advance the syringe 114 from its retracted position to its extended position and discharge its contents through the needle 118. The drive accomplishes this task by acting directly on the drug and the syringe 114. Static friction between the drive coupling 134 and the syringe body 116 initially ensures that they advance together, until the return spring 126 bottoms out or the syringe body 116 meets some other obstruction (not shown) that retards its motion.

The multi-component drive between the drive spring 130 and the syringe 114 consists of three principal components. A drive sleeve 131 takes drive from the drive spring 130 and transmits it to a drive element 132. This in turn transmits drive to the drive coupling 134 already mentioned.

A trigger 214 is provided on the housing 112 remote from the exit aperture 128. The trigger, when operated, serves to decouple the drive sleeve 131 from the housing 112, allowing it to move relative to the housing 112 under the influence of the drive spring 130. The operation of the device is then as follows.

The actuator is then depressed and the drive spring 130 is released. The drive spring 130 moves the drive sleeve 131, the drive sleeve 131 moves the drive element 132 and the drive element 132 moves the drive coupling 134. The drive coupling 134 moves and, by virtue of static friction and hydrostatic forces acting through the drug to be administered, moves the syringe body 114 against the action of the return spring 126. The syringe body 114 moves the syringe carrier 150, which in turn moves the return spring support and compresses the return spring 126. The hypodermic needle 118 emerges from the exit aperture 128 of the housing 112. This continues until the return spring 126 bottoms out or the syringe body 116 meets some other obstruction (not shown) that retards its motion. Because the static friction between the drive coupling 134 and the syringe body 116 and the hydrostatic forces acting through the drug to be administered are not sufficient to resist the full drive force developed by the drive spring 130, at this point the drive coupling 134 begins to move within the syringe body 116 and the drug begins to be discharged. Dynamic friction between the drive coupling 134 and the syringe body 116 and hydrostatic and hydrodynamic forces now acting through the drug to be administered are, however, sufficient to retain the return spring 126 in its compressed state, so the hypodermic needle 118 remains extended.

Before the drive coupling 134 reaches the end of its travel within the syringe body 116, so before the contents of the syringe have fully discharged, flexible latch arms linking the first and drive couplings 132, 134 reach an interchangeable release element 155 connected to the distal end of the syringe carrier 150.

The interchangeable release element 155 is essentially a constriction which moves the flexible latch arms to a position so that they no longer couple the drive element 132 to the drive coupling 134. Once this happens, the drive element 132 acts no longer on the drive coupling 134, allowing the drive element 132 to move relative to the drive coupling 134. Consequently, the drive coupling 134 continues to move within the syringe body 116 and the drug continues to be discharged. Thus, the return spring 126 remains compressed and the hypodermic needle remains extended.

After a time, the drive coupling 134 completes its travel within the syringe body 116 and can go no further. At this point, the contents of the syringe 114 are completely discharged and the force exerted by the drive spring 130 acts to retain the drive coupling 134 in its terminal position, allowing the drive element 132 to continue its movement.

Flexible latch arms linking the drive sleeve 131 with the drive element 132 reach another constriction within the housing 112. The constriction moves the flexible latch arms so that they no longer couple the drive sleeve 131 to the drive element 132. Once this happens, the drive sleeve 131 acts no longer on the drive element 132, allowing them to move relative each other. At this point, the forces developed by the drive spring 130 are no longer being transmitted to the syringe 114. The only force acting on the syringe will be the return force from the return spring 126 which acts on the end of the syringe 114 nearest to the needle 118 via the return spring support and the syringe carrier 150. Consequently, the syringe is returned to its retracted position and the injection cycle is complete.

The interchangeable release element 155 is provided with flexible arms 271 for connecting the interchangeable release element 155 to the syringe carrier 150 at cut-outs 281 on the syringe carrier 150.

Figure 3C:
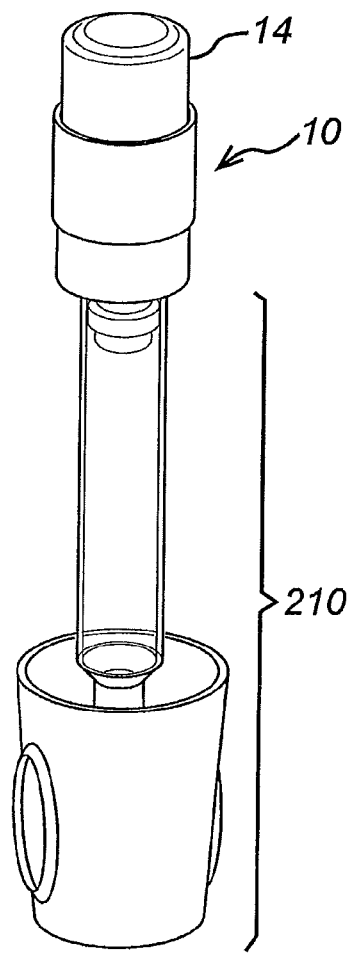

FIGS. 3*a* to 3*c* show a fluid transfer assembly 10 having a first open end 11 which is adapted to receive a vial 14 containing fluid. The fluid transfer assembly 10 also has a second open end 12 which is adapted to be attached to delivery assembly 210 without interchangeable release element 155 connected to the syringe carrier 150. The second open end 12 has a diameter smaller than the first open end 11. The fluid transfer assembly can be cylindrical in shape and formed from a plastic type material.

The first open end 11 also comprises a hollow needle 13, which, when a vial is attached to the first open end 11, acts to pierce a seal 14*a* on the vial. The needle 13 forms the fluid pathway between the two ends 11, 12. The seal, as on most types of vial, is formed from breachable material, one type of material that could be used is metallic foil.

The vial can be attached to the first open end 11 and held by the cylindrical walls of the fluid transfer system. The second open end 12 can be attached to the delivery assembly 210, as shown in FIG. 3*c*, with the first open end 11 above the second open end 12 with respect to ground, the fluid can then flow from the vial under the force of gravity into the syringe body 116 through the fluid pathway formed by the needle 13 and the second open end 12.

Figure 4:
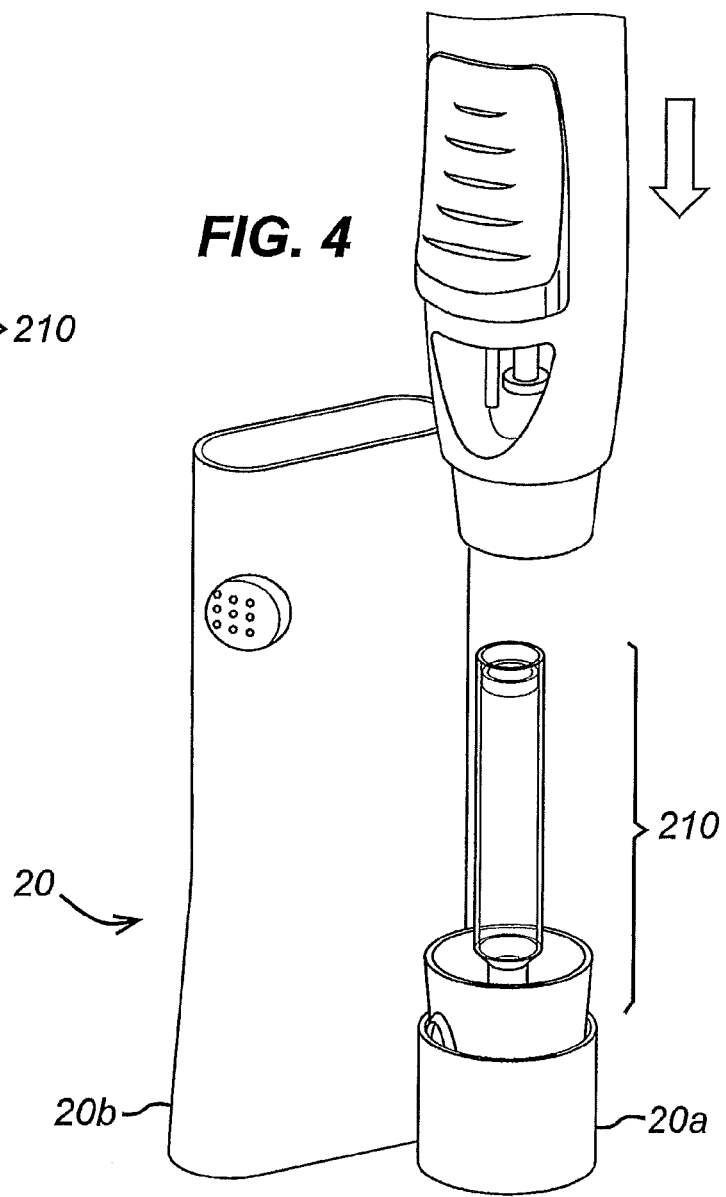
FIG. 4 shows a perspective view of a fluid transfer system according to the present invention.

FIG. 4 shows a base station 20 for use in conjunction with the injection device 110 and transfer assembly 10 and vial 14 of the present invention. The base station 20 comprises two sections 20*a* and 20*b*. Section 20*a* of the base station 20 is sized and dimensioned to support the delivery sub-assembly 210 and section 20*b* is adapted to reset the drive sub-assembly 220. The section 20*b* comprises a protrusion (not shown) which acts on the extended drive of the injection device (after use) to force it to retract and be reset. The transfer assembly 10 described above is placed on the open end of the delivery subassembly 210 whilst it is held in place on the base station 20. Once the fluid from the vial 14 has been transferred to the syringe, the fluid transfer assembly is removed from the delivery assembly 210, the interchangeable release element 155 is attached to the top of the syringe carrier 150 on the delivery assembly 210 and the reusable drive assembly 220 is inserted over the delivery assembly 210 to form a delivery device 110 which can then be removed from the base station 20.

It will of course be understood that the present invention has been described above purely by way of example and modifications of detail can be made within the scope of the invention.

The invention claimed is:

1. An injection kit comprising:
   a fluid transfer assembly comprising:
   means for connection to a syringe;
   means for receiving a vial having a closure element,
   wherein the receiving means is adapted to engage and open the closure element and permit fluid in the vial to be transferred to the syringe from the vial, wherein the connection means comprises an end of the fluid transfer assembly which is open and dimensioned to fit over or in an open end of the syringe body which is opposite a needle end of the syringe, wherein the fluid transfers in use from the vial to the syringe under the force of gravity, when the receiving means is located above the connection means;
   a syringe;
   a delivery device including a delivery sub-assembly and a drive sub-assembly, which are both adapted to be attached to the syringe, and operate together to deliver the fluid from the syringe; and
   a base station which is adapted to receive the drive sub-assembly and reset the drive by moving it from its second position to its first position and reset the release mechanism such that when actuated again it releases the drive.

2. The kit of claim 1 wherein the base station comprises an attachment to hold the delivery sub-assembly.

\* \* \* \* \*